US011199953B2

(12) United States Patent
Unger (10) Patent No.: US 11,199,953 B2
(45) Date of Patent: Dec. 14, 2021

(54) PROCESSING A USER INPUT IN RELATION TO AN IMAGE (71) Applicant: Siemens Healthcare GmbH, Erlangen (DE)

(72) Inventor: Milan Unger, Kvetoslavov (SK)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/554,859

(22) Filed: Aug. 29, 2019

(65) Prior Publication Data
US 2020/0073537 A1 Mar. 5, 2020

(30) Foreign Application Priority Data
Aug. 30, 2018 (EP) .................................. 18191732

(51) Int. Cl.
G06F 3/0484 (2013.01)
G06F 3/0488 (2013.01)
A61B 8/00 (2006.01)
G06F 3/0482 (2013.01)
G06T 11/60 (2006.01)
G16H 30/40 (2018.01)

(52) U.S. Cl.
CPC .......... *G06F 3/04842* (2013.01); *A61B 8/468* (2013.01); *G06F 3/0482* (2013.01); *G06F 3/04845* (2013.01); *G06F 3/04883* (2013.01); *G06T 11/60* (2013.01); *G16H 30/40* (2018.01)

(58) Field of Classification Search
CPC ............. G06F 3/04842; G06F 3/04845; G06F 3/0482; G06F 3/04883; A61B 8/468; G06T 11/60; G16H 30/40
See application file for complete search history.

(56) References Cited

U.S. PATENT DOCUMENTS

2008/0304698 A1* 12/2008 Rasmussen ........ G06K 9/00402
382/100
2013/0198687 A1* 8/2013 Bird ..................... A61B 5/7435
715/810
2014/0201672 A1 7/2014 Borzello et al.
(Continued)

OTHER PUBLICATIONS

Google Creative Lab "AutoDraw" VIDEO, Apr. 2017; https://experiments.withgoogle.com/autodraw; screenshot from Jun. 28, 2018.
(Continued)

Primary Examiner — Roberto Borja
(74) Attorney, Agent, or Firm — Harness, Dickey & Pierce, P.L.C.

(57) ABSTRACT

A method is for processing a user input in relation to an image. In an embodiment, the method includes receiving first input data derived from user input in relation to a first image, the first input data indicating a selection of at least a part of the first image; performing a determination process to determine, at least partly based upon the first input data received and previous action data, one or more candidate actions to perform in relation to the first image, the previous action data relating to previous image processing actions performed in relation to one or more images; and providing output data indicating at least a first action of the one or more candidate actions determined.

24 Claims, 4 Drawing Sheets

(56) References Cited

U.S. PATENT DOCUMENTS

| | | | |
|---|---|---|---|
| 2014/0237425 A1* | 8/2014 | Chan | G06F 3/0482 715/810 |
| 2014/0280113 A1* | 9/2014 | Hohwald | G06F 16/5866 707/728 |
| 2015/0026642 A1* | 1/2015 | Wilson | G06F 9/451 715/825 |
| 2016/0320926 A1 | 11/2016 | Ganin et al. | |
| 2017/0143310 A1* | 5/2017 | Bo | G16H 40/63 |
| 2017/0154261 A1* | 6/2017 | Sunehag | G06N 3/08 |
| 2019/0384622 A1* | 12/2019 | Chen | G06F 3/0482 |

OTHER PUBLICATIONS

Preetha, M. Mary Synthuja Jain et al. "Firefly Based Region Growing and Region Merging for Image Segmentation" International Conference on Emerging Technological Trends [ICETT]—2016.

Li, Yin et al. "Lazy Snapping" ACM Transactions on Graphics, vol. 23, No. 3, pp. 303-308, Aug. 2004 // DOI:10.1145/1015706.1015719.

Stefano, Alessandro et al. "A Fully Automatic Method for Biological Target Volume Segmentation of Brain Metastases" International Journal of Imaging Systems and Technology, vol. 26, No. 1, pp. 29-37, 2016.

Microsoft Research "Tech Showcase: Project InnerEye—Assistive AI for Cancer Treatment" VIDEO, Oct. 2, 2017; on: https://channel9.msdn.com/Shows/Microsoft-Research/Tech-ShowcaseProject-InnerEye--Assistive-AI-for-Cancer-Treatment; screenshot from Jun. 28, 2018.

Dorgham, O. M. "Automatic Body Segmentation from Computed Tomography Image" 3rd International Conference on Advanced Technologies, for Signal and Image Processing—ATSIP'2017, May 22-24, 2017.

Xiyu, Yu et al. "Supervised Image Segmentation using Learning and Merging" 8th International Symposium on Image and Signal Processing and Analysis (ISPA 2013), Sep. 4-6, 2013.

Ho, Seng-Beng "On Effective Causal Learning" International Conference on Artificial General Intelligence, vol. 8598, pp. 43-52, 2014.

Rother, Carsten et al. ""GrabCut"—Interactive Foreground Extraction using Iterated Graph Cuts" ACM Transactions on Graphics, vol. 23, No. 3, Aug. 2004.

Ho, Seng-Beng "Deep Thinking and Quick Learning for Viable AI" Future Technologies Conference 2016 (FTC 2016), Dec. 6-7, 2016.

Cohen, Jonathan D. et al. "Should I stay or should I go? How the human brain manages the trade-off between exploitation and exploration" Philosophical Transcations of the Royal Society; vol. 362; pp. 933-942; 2007; doi:10.1098/rstb.2007.2098.

European Search Report for European Patent Application No. EP18191732.9 dated Feb. 26, 2019.

European Office Action dated Oct. 30, 2019.

* cited by examiner

PROCESSING A USER INPUT IN RELATION TO AN IMAGE

PRIORITY STATEMENT

The present application hereby claims priority under 35 U.S.C. § 119 to European patent application number EP 18191732.9 filed Aug. 30, 2018, the entire contents of which are hereby incorporated herein by reference.

FIELD

Embodiments of the invention relate to methods, apparatus and computer program products for processing a user input in relation to an image.

BACKGROUND

Image processing applications often permit users to select one or more portions of an image and provide image processing functions for processing selected portions to modify the image in some way or to provide information regarding the selected portions to the user.

For example, a user may operate an input device, such as a mouse, stylus or touch-screen, to indicate a region of interest within an image by defining a contour around a portion of the image using the input device.

Using the input device, the user may then select one or more image processing functions that are applied to the image or the selected portion of the image. For example, the user may select commands or settings by selecting menu options displayed in a system of menus, icons displayed in toolbars, shortcuts, or by providing textual input or voice input. Such selections represent an intent of the user. Intent is defined herein as the image processing function intended by the user to be performed and may include the selection of a region of interest in the image.

In order for the user to select features within the image with a precision corresponding to the resolution of the image (i.e. near-pixel level precision), some image processing apparatus may provide a specialized input device that, for example, enables the user to visualize and track the position of the input device with an appropriate precision. Alternatively, the user may provide multiple user inputs to iteratively zoom in on a region of the image to select a feature with the appropriate precision. Such multiple inputs reduce the efficiency of the image processing and may cause users to restrict use of certain capabilities of the image processing application and use only a limited subset of the application capabilities. In the case of touchscreen user interfaces, using a stylus or finger gesture of the user, near-pixel level precision is difficult to achieve.

To overcome these difficulties, certain techniques have been developed to estimate the intended input. For example, edge snapping techniques based on so-called "Lazy Snapping" and "GrabCut" algorithms have been used to enable a user to indicate a region of interest by rough gesture. Other techniques involve delineation of region of interest using a region growing algorithm to expand a single user input (e.g. a mouse click or tap gesture) to cover a region of interest.

SUMMARY

The inventors have discovered that such techniques may be inaccurate for delineating regions of interest with complex shapes and may require parameters that are configured for specific image features (e.g. specific anatomical features) and/or image characteristics, to provide appropriate results.

Accordingly, problems are solved or mitigated in embodiments of the present application including a method, an image processing apparatus, and a computer program product/readable medium. The claims are related to further aspects of the invention.

The invention relates in one embodiment, to a method of processing a user input in relation to an image, comprising:
receiving first input data derived from user input in relation to a first image, the first input data indicating a selection of at least a part of the first image;
performing a determination process to determine, at least partly based upon the first input data received and previous action data, one or more candidate actions to perform in relation to the first image, the previous action data relating to previous image processing actions performed in relation to one or more images; and
providing output data indicating at least a first action of the one or more candidate actions determined.

The invention relates in one embodiment to an image processing apparatus comprising:
an associative memory arranged to receive first input data derived from a user input in relation to a first image, the first input data indicating a selection of at least a part of the first image and previous action data relating to previous image processing actions performed in relation to one or more images; and
a processor arranged to:
determine, at least partly on the basis of the first input data and previous action data, one or more candidate actions to perform in relation to the first image; and
provide output data indicating at least a first action of the one or more candidate actions.

The invention relates in one embodiment to a computer program, the computer program being loadable into a memory unit of a data processing system, including program code sections to make a data processing system execute the method according to an embodiment of the invention when the computer program is executed in the data processing system.

The invention relates in one embodiment to a non-transitory computer program product storing a computer program, loadable into a memory of a data processing system, including program code sections to make a data processing system execute the method of an embodiment when the computer program is executed in the data processing system.

The invention relates in one embodiment to a non-transitory computer readable medium storing a computer program, loadable and executable by a data processing system, including program code sections which, upon execution by the data processing system, cause the data processing system to perform the method of an embodiment.

The invention will be illustrated below with reference to the accompanying figures using example embodiments. The illustration in the figures is schematic and highly simplified and not necessarily to scale.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention relates in one embodiment, to a method of processing a user input in relation to an image, comprising:

receiving first input data derived from a user input in relation to a first image, the first input data indicating a selection of at least a part of the first image;

performing a determination process to determine, at least partly on the basis of the first input data and previous action data, one or more candidate actions to perform in relation to the first image, the previous action data relating to previous image processing actions performed in relation to one or more images; and providing output data indicating at least a first action of the one or more candidate actions.

One embodiment of the invention relates in one aspect to a method wherein the previous image processing actions comprise one or more of: an annotation; a measurement; and a highlighting.

One embodiment of the invention relates in one aspect to a method wherein the determination process comprises determining, at least partly on the basis of previous image parts in relation to which the previous actions were performed, a part of the first image in relation to which an action is to be performed.

One embodiment of the invention relates in one aspect to a method wherein the first input data comprises:

one or more user input characteristics of the user input, the one or more user input characteristics comprising at least one of: a location of the input in the first image; a shape of an input gesture; and a dimension of an input gesture; and one or more image characteristics of the one or first image, the one or more image characteristics comprising at least one of: a dimension of the first image; one or more display characteristics of the first image; and one or more display characteristics in a selected part of the image.

One embodiment of the invention relates in one aspect to a method wherein the first image comprises an image of a patient, and the first input data comprises at least one of: a modality of the first image; and data relating to the patient.

One embodiment of the invention relates in one aspect to a method wherein the determination process comprises:

an identification process to identify the previous action data by retrieving data relating to previous actions from a memory, based on the first input data;

a selection process to select one or more processing algorithms for processing the first image to generate the one or more candidate actions; and an evaluation process to evaluate the one or more candidate actions.

One embodiment of the invention relates in one aspect to a method wherein the memory comprises a heterogenous associative memory.

One embodiment of the invention relates in one aspect to a method wherein the previous action data indicates input data relating to previous actions and processing algorithms used to generate candidate actions from which the previous actions were selected, and the selection process comprises:

a comparison process to compare the first input data with input data relating to the previous actions; and selecting one or more processing algorithms, at least partly on the basis of the comparison process, from processing algorithms used to generate candidate actions from which the previous actions were selected.

One embodiment of the invention relates in one aspect to a method wherein the selection process comprises a random or pseudo-random process for selecting processing algorithms.

One embodiment of the invention relates in one aspect to a method wherein the one or more processing algorithms comprises at least one of: an image filter algorithm; and an automatic segmentation algorithm.

One embodiment of the invention relates in one aspect to a method wherein the previous action data comprises heuristics data relating to heuristics used to evaluate the previous actions, and the evaluation process comprises:

identifying one or more heuristics to evaluate a respective candidate action.

One embodiment of the invention relates in one aspect to a method wherein the evaluation process comprises generating a probabilistic value in relation to each respective candidate action indicative of a probability that the candidate action corresponds to an intended action.

One embodiment of the invention relates in one aspect to a method wherein the probabilistic value is derived based on at least one of a plausibility value and a confidence value.

One embodiment of the invention relates in one aspect to a method comprising receiving a user selection of the first action and storing data relating to first action in the memory as previous action data.

The invention relates in one embodiment to an image processing apparatus comprising:

an associative memory arranged to receive first input data derived from a user input in relation to a first image, the first input data indicating a selection of at least a part of the first image and previous action data relating to previous image processing actions performed in relation to one or more images; and a processor arranged to:
 determine, at least partly on the basis of the first input data and previous action data, one or more candidate actions to perform in relation to the first image; and
 provide output data indicating at least a first action of the one or more candidate actions.

The invention relates in one embodiment to a computer program, the computer program being loadable into a memory unit of a data processing system, including program code sections to make a data processing system execute the method according to an embodiment of the invention when the computer program is executed in the data processing system.

The computer program product or medium store, for example, a computer program or comprise another element apart from the computer program. This other element can be hardware, for example a memory device, on which the computer program is stored, a hardware key for using the computer program and the like, and/or software, for example a documentation or a software key for using the computer program.

The image processing may be performed on any image but in certain examples may be performed on a medical image. For example, the image may be acquired by a medical imaging device selected from the group consisting of an X-ray fluoroscopy device, a computed tomography device, a magnetic resonance imaging device, a molecular imaging device, a SPECT-device, a PET-device and combinations thereof. The medical imaging device can be, for example, a combination of an imaging modality and a therapy modality, in particular a radiation therapy modality.

Reference is made to the fact that the described methods and the described image processing apparatus are merely preferred example embodiments of the invention and that the invention can be varied by a person skilled in the art, without departing from the scope of the invention provided it is specified by the claims.

The invention will be illustrated below with reference to the accompanying figures using example embodiments. The illustration in the figures is schematic and highly simplified and not necessarily to scale.

Figure 1:
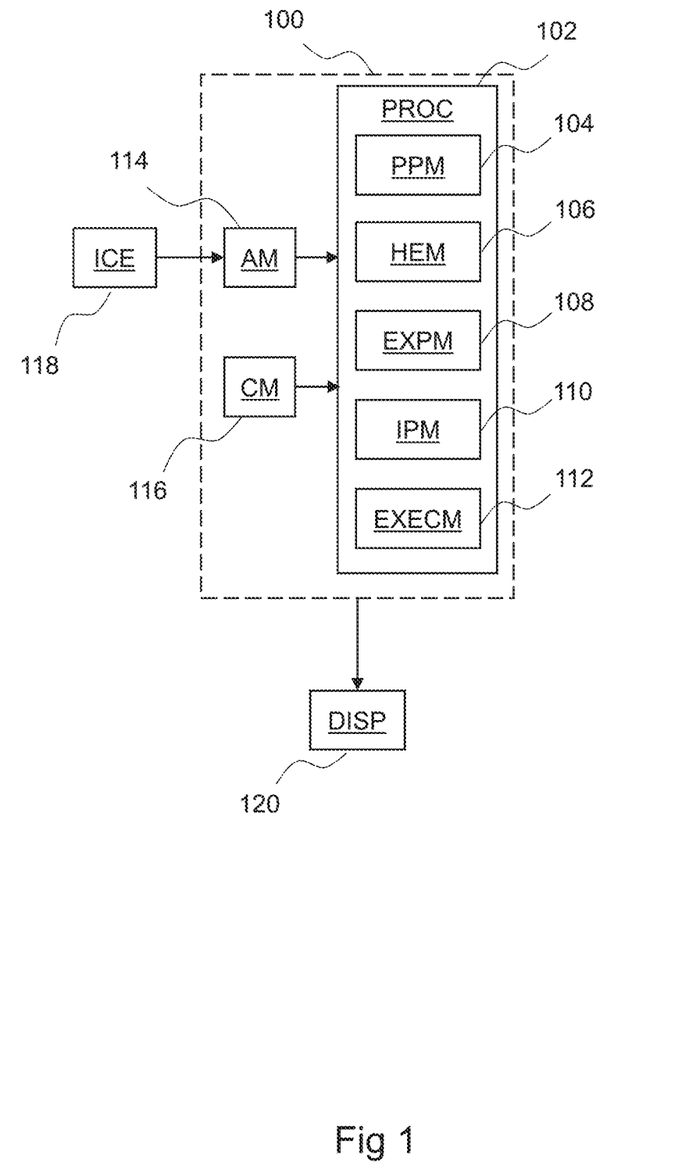
FIG. 1 is a schematic diagram of an image processing apparatus according to one embodiment of the invention.

FIG. 1 is a diagram illustrating an image processing apparatus 100 according to an embodiment of the present invention. The image processing apparatus 100 comprises a processor (PROC) 102 for processing a user input in relation to an image according to the methods described herein.

The processor 102 may run a program implementing various modules. As shown in FIG. 1, the modules may include a pre-processing module (PPM) 104, a hypothesis evaluation module (HEM) 106, an exploration module (EXPM) 108, an intent presentation module (IPM) 110, and an execution module (EXECM) 112.

The pre-processing module 104 prepares the data it receives for further evaluation. In particular, the preprocessing module 104 receives data relating to a current image and corresponding user input and data relating to previously processed images and their corresponding inputs. The pre-processing module 104 also receives data relating to the actual image processing algorithm that was implemented (i.e. the image processing function performed) for each of the previously processed images and data relating to candidate algorithms that were evaluated to be plausible when those images were processed but were determined to not correspond with the intent of the user. The preprocessing module 104 generates, based on the data it receives in relation to current and previous images, a set of algorithms which may be applied to process the current image.

The hypothesis evaluation module 106 evaluates results of algorithms generated, and to be executed, by the preprocessing module 104 to derive plausibility values for each of the algorithms that represent possible intents of the user {i.e. possible regions of interest and possible corresponding actions intended by the user by user input).

The exploration module 108 randomizes selection of the preprocessing steps, algorithms, and control parameters. For example, the exploration module 108 may select, on a random or pseudo-random basis, preprocessing steps, algorithms and other parameters to generate potential actions that otherwise would not be available to the image processing apparatus (for example, because the image processing apparatus had not experienced a particular set or pattern of inputs previously). For example, the exploration module 108 may randomly pick a method of delineation of the region of interest by, for example, setting a random edge thresholding value. In another example, the exploration module 108 may select a random action to be performed in respect of the image that would be evaluated alongside actions determined based on previous experience. This enables the image processing apparatus 100 to consider and evaluate possible actions that have not previously been experienced.

The intent presentation module 110 performs an intent presentation and explanation process as described below with reference to FIG. 3. In particular, the intent presentation and explanation module 110 presents the user with a selection of actions which are determined to be likely to correspond with the intention of the user in providing a given user input to select a portion of the image.

The execution module 112 executes the action determined to be the action intended by the user.

In an example, the image processing apparatus 100 comprises an associative memory (AM) 114. Whereas conventional computing memory, such as random-access memory (RAM), stores data at a unique address and can recall the data upon presentation of the complete unique address, the associative memory 114 is a content-addressable structure that associates two patterns such that when one of the patterns is presented, the other pattern can be recalled.

The associative memory 114 comprises two layers of neurons: an input layer and an output layer. Each of the neurons in the input layer is connected to each of the neurons in the output layer via synapses. Each synapse can be assigned a weighting for its corresponding pair of input and output neurons. Patterns received at the neurons of the input layer produce a pattern at the neurons of the output layer according to the weightings. The weightings of each of the synapses of the associative memory 114 may be developed over time by learning based on receipt of new patterns at the input layer neurons. The learning provides storage of a large set of activity patterns.

In some examples, the associative memory 114 may be a hetero-associative memory, meaning that the number of neurons in the input layer may be different to the number of neurons in the output layer. For example, in a heteroassociative memory, a retrieved pattern (i.e provided by the output layer) is, in general, different from the input pattern (i.e. that provided to the input layer) not only in content but possibly also in type and format.

The image processing apparatus 100 may also comprise conventional memory (CM) 116. The conventional memory 116 may be any suitable form of memory. For example, the conventional memory 116 may comprise volatile memory, such as random-access memory (RAM) and/or non-volatile memory such as read only memory (ROM) or flash memory. Furthermore, the conventional memory 116 might comprise multiple, separate, memory devices and may comprise a combination of volatile and non-volatile memory. In some examples, certain components of the invention may be stored in one memory device, while other components may be stored in another memory device.

The conventional memory 116 may store a computer program executable by the processor 102, to perform the methods described herein, and specifically the methods described below with reference to FIGS. 2 and 3.

The processor 102 is arranged to receive input data derived from user input in relation to images from a user input interface (ICE) 118. For example, the processor 102 may receive input data derived from user input indicating a selection of a part of an image.

In some examples, programs running on the processor 102 can process user input obtained from the user input interface 118 that receives user input from a user input device or devices (not shown). User input devices may include a mouse or stylus, or any other pointer device, which may be incorporated within a computing device comprising the image processing apparatus 100 or may be connected to it via a wired or wireless connection. In some examples, user input functions may be combined with functions of a display as a touch-screen display. The touch-screen display may be touched by a user using a finger in order to generate and provide user input data that is received by the processor 102 and then processed by one or more programs running on the processor 102. Alternatively, a stylus or other device may be used to provide the touch input. The touch-screen display may use any of a number of different touch-sensing technologies including capacitive sensing technologies such as mutual capacitance or self capacitance, where a number of capacitive sensor elements detect touch input to the touch-screen display.

The processor 102 may control images presented on a display (DISP) 120 and may be arranged to generate display data, based on image data generated by the methods described herein, for controlling display parameters of the display 120.

The methods described herein enable a user to identify a region of interest in an image using a user input (such as a single tap or mouse click, or a gesture roughly representing the area of interest), and for the image processing apparatus 10 to determine the most plausible parameters for delineation of a region of interest (i.e. to correspond with the region that the user intended to select) and the most plausible parameters relating to the intention(s) of the user regarding image processing functions to be applied to the region that the user intended to select. This may mitigate a need for the user input to be precise (for example, to precisely demarcate a region of interest) The plausibility of the parameters for delineating the region of interest and relating to the intention of the user is evaluated with respect to the given situation (i.e. as provided by current inputs) as well with respect to context (i.e. provided by previous experience of the image processing apparatus 100) using a combination of computer vision, machine learning, and/or artificial intelligence techniques. The image processing apparatus 100 adapts to user feedback by integrating its experience from user feedback into the hetero-associative memory 114. In particular, the associative memory 114 is arranged to receive data relating to a current image processing operation as well as data relative to previous image processing operations.

Figure 2:
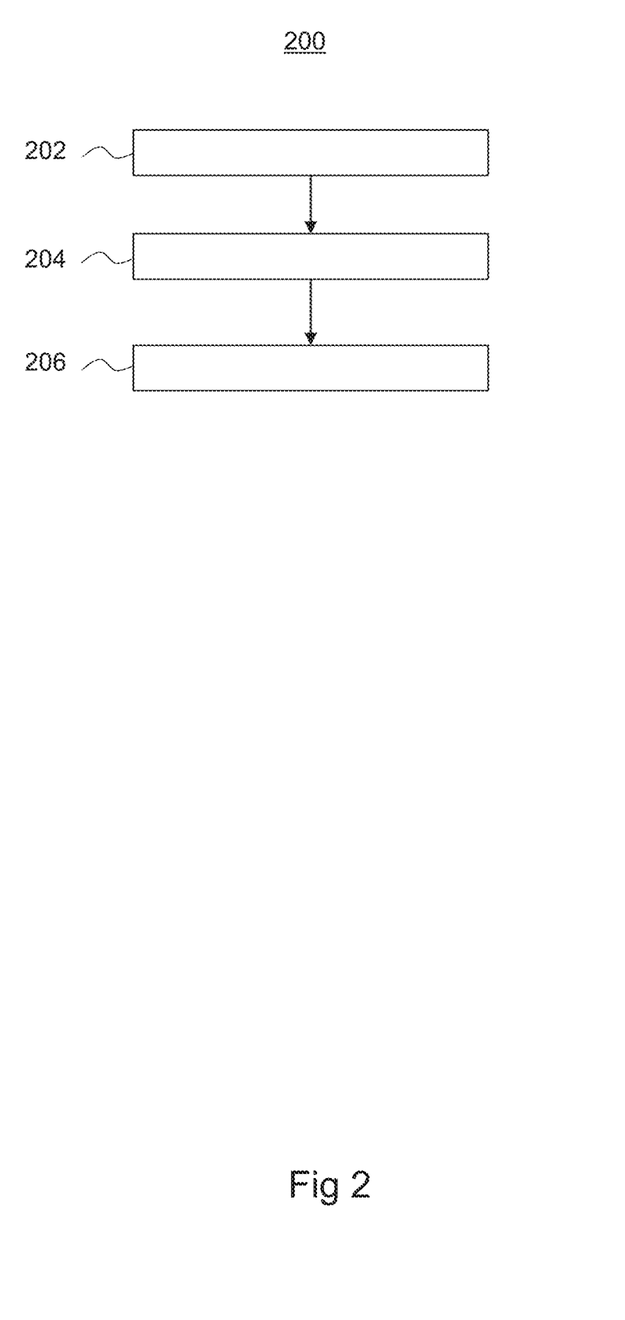
FIG. 2 is a simplified workflow diagram illustrating a method according to one embodiment of the invention.

FIG. 2 is a flow diagram depicting a method 200 of processing a user input in relation to an image. The method 200 may, for example, be implemented by software or firmware executed by the processor 102 described above with reference to FIG. 1.

At block 202 first input data derived from a user input in relation to a first image is received. The first input data indicates a selection of at least a part of the first image. For example, as described above the first image may be a medical image, such as an image of a patient or part of a patient. For example, the image may be an image showing one or more anatomical structures within the patient.

The user input may comprise a location of the input in the first image, a shape of an input gesture, and/or a dimension of an input gesture. The user input data may also comprise one or more image characteristics of the one or first image, the one or more image characteristics. The image characteristics may be one or more of: a dimension of the first image, one or more display characteristics of the first image, and one or more display characteristics in a selected part of the image.

At block 204, a determination process is performed to determine, at least partly on the basis of the first input data and previous action data, one or more candidate actions to perform in relation to the first image. The previous action data relates to previous image processing actions performed in relation to one or more images. For example, the previous image processing actions comprise one or more of: an annotation; a measurement; and a highlighting.

For example, a user may provide a user input (for example by a mouse click to select an apparently calcified cardiac vessel). In response to such a selection, the processor 102 may determine the intention of the user based on the user input and previous experience of similar user inputs in similar contexts. For example, the processor 102 may determine that, the user input is intended to delineate the vessel and calculate or measure a degree of calcification. In another example, the processor 102 may determine that the user intended to determine and identify a centre line of a calcified cardiac vessel, thereby allowing a physician to navigate along the respective blood vessel.

In another example, relating to mammography, a user may provide a user input (for example by mouse clicks or touch screen gesture) to select areas of the image that appear to show abnormal or suspicious tissue structures. In response to such a selection, the processor 102 may delineate a structure relating to the structure the user intended to select the structure and perform a so-called "BI-RADS" (Breast Imaging Reporting and Data System) calculation in which the results of the scan are categorised accordingly. In another example, the algorithm may determine that the intention of the user is to determine a report with respect to previous images and prepare a follow-up report reporting a change in the size or other characteristic of the tumor. In another example, the processor 102 may determine from the user input that the user intended to identify (for example, with annotations) possible metastases of a primary tumor.

The determination process may include, for example, determining, a part of the first image in relation to which an action is to be performed, at least partly on the basis of previous image parts in relation to which previous actions were performed.

In some examples, the determination process may comprise an identification process to identify previous action data by retrieving data relating to previous actions.

The determination process may also include a selection process for selecting one or more processing algorithms for processing the current image so as to generate one or more candidate actions which could be performed in respect of the current image.

The selection process may comprise comparing current input data with input data relating to previous actions and selecting a processing algorithm (or algorithms) based on the comparison process, from processing algorithms used to generate candidate actions from which the previous actions were selected. For example, the processing algorithm may be an image filter algorithm or an automatic segmentation algorithm. For example, the processing algorithm may be an algorithm to remove bone features from an image, or more generally to subtract or fuse features of an image. In other examples, the processing algorithm may be arranged to register the image with a previously acquired image. In other examples, the processing algorithm may be arranged to label pixels; for example, the processing algorithm may be arranged to label pixels according to the part of a patients anatomy (i.e. pixels may be labelled as being tissue from e.g. the brain, heart, abdomen, lungs, bone, blood vessel etc.) In other examples, the processing algorithm may be arranged to label pixels according to whether the respective pixel is determined to be part of a tumor or not, or part of an inflamed piece of tissue or not. In other examples, the processing algorithm may be arranged to determine the type of image (e.g. whether the image is that of a patient's head or a patient's abdomen) or to determine characteristics of the patient (e.g. whether the patient is male or female and/or an adult or a child). The selection process may also comprise a random or pseudo-random process for selecting processing algorithms.

The determination process may also include an evaluation process to evaluate each of the candidate actions. For example, the candidate actions may be evaluated to generate a short list of candidate actions which are most likely to correspond with the intended action of the user.

The previous action data indicates input data relating to actions and processing algorithms that were previously implemented and used to generate candidate actions from which the previous actions were selected. The previous action data may, for example, include heuristics data relating to heuristics used to evaluate the previous actions, and the evaluation of each of the candidate action may involve identifying one or more heuristics with which to evaluate a respective candidate action.

At block 206, providing output data is provided that indicates at least a first action of the one or more candidate actions.

Figure 3:
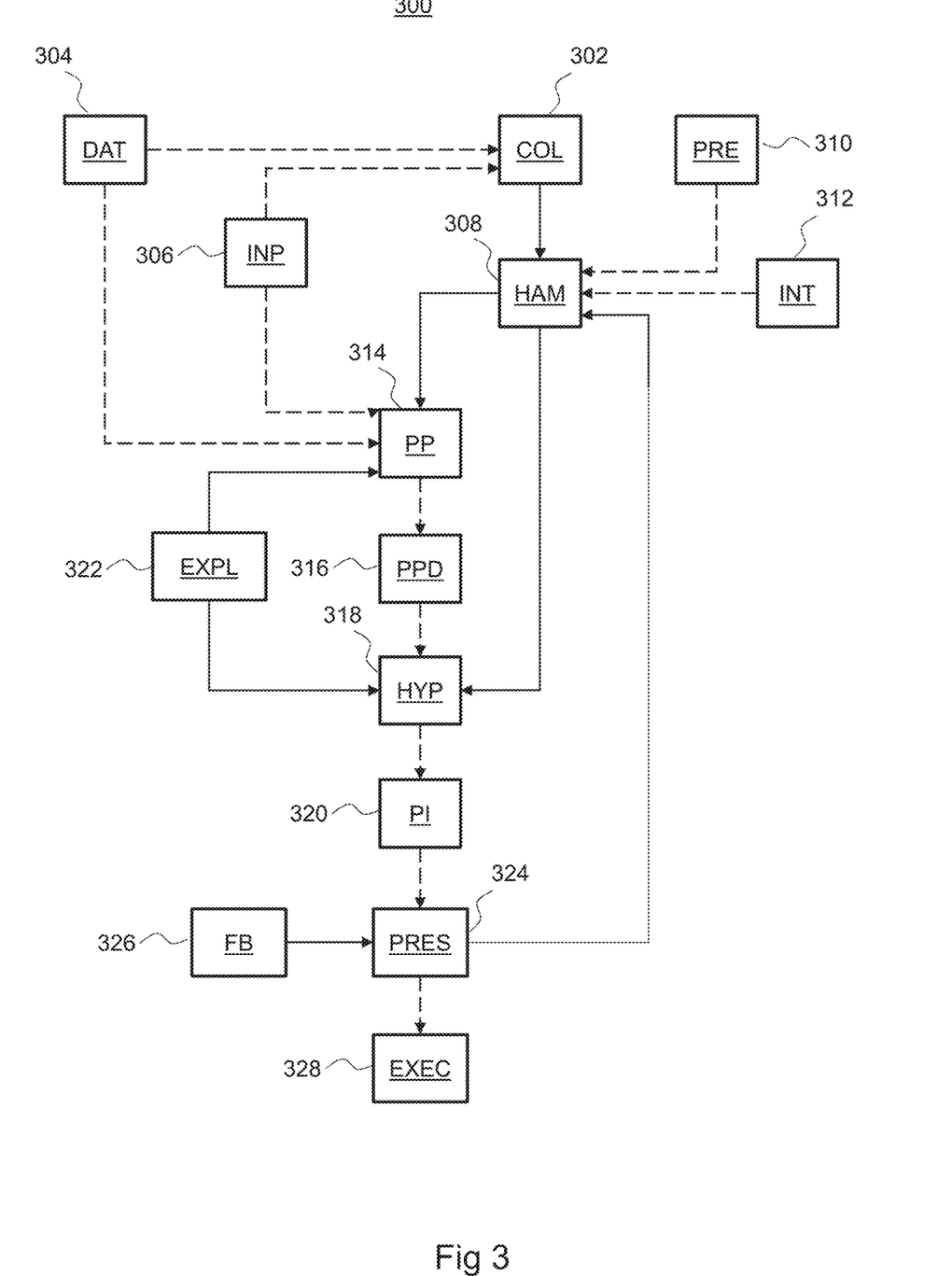
FIG. 3 is a schematic diagram illustrating the operation of an image processing apparatus.

FIG. 3 is a schematic diagram illustrating the operation 300 of an image processing apparatus such as the image processing apparatus 100 described above with reference to FIG. 1.

An input collection and encoding process (COL) 302 receives input data (DAT) 304 comprising raw image data and meta data and user input data (INP) 306 representative of user input, such as gestures or other interactions between the user and the image processing apparatus 100. The meta data may comprise, for example, data representative of properties of the image such as the modality with which the image was acquired, the type of image, imaging parameters used when acquiring the image, and an indication of whether contrast agent was present when the image was acquired. The meta data may also comprise data representing patient characteristics and/or data indicative of a clinical question, a medical history of the patient, and/or a reason for admitting the patient to hospital.

The user input data 306 is derived from signals from a user input device and received at the user input interface 118 and may be determined based on, for example, a distribution of pixel intensities in the vicinity of a user input action or gesture.

The input collection and encoding process 302 collects and encodes received data into an appropriate form in which a hetero-associative memory (HAM) 308 (which may correspond to the associative memory 114 described above with reference to FIG. 1) can process the data.

Initially, the image processing apparatus 100 may have no previous experience of performing determination processes to determine actions in relation to images on the basis of user input. Accordingly, in response to processing image data and user input, the associative memory 114 generates an empty list of likely user intentions.

In subsequent operations, which may be referred to as a recall phase (e.g. when a user has previously interacted with the image processing apparatus 100), the associative memory 114 retrieves and identifies previous episode data (PRE) 310 relating to previous image processing operations referred to hereinafter as episodes. An episode is defined herein as an operation of the image processing apparatus 100 in which output data indicating at least one action is provided for a given image and user input. Accordingly, the previous episode data (PRE) 310 (previous action data) is representative of previous episodes of user intent detection and is selected based on a similarity of current user input data (and/or image data and meta data) and user input data received in a previous episode. In particular, the previous episode data 310 represents actual intended actions of the user (represented by user input) in respect of a respective image. That is, the actual portion of the image that the user intended to select and the corresponding image processing function that the user intended to be performed on the selected portion of the image.

The previous episode data 310 may, for example, include information relating to the type of a previous image, information regarding what parts of previous images were selected, information relating to what structure the previous image was imaging (for example, that the image was an image of a particular anatomical structure), and information regarding what the intent of the user was in relation to the previous image (for example, that the user intended to measure a dimension of the structure). In some examples, the previous episode data 310 may also include, for example, information regarding what preprocessing tasks were executed to prepare the input data (i.e. the image data, meta data and user input data) for further evaluation and information about algorithms used for evaluation of the user's intent.

The associative memory 114 may also retrieve user intent data (INT) relating to intentions of the user that were considered by the image processing apparatus 100 in relation to respective previous episodes, but which did not represent the actual intended action of the user.

The associative memory 114 may provide multiple previous episodes that correspond to the current input data derived from user input in relation to images in terms of similarity with the current input data. Accordingly, there may be multiple candidate processing algorithms (candidate actions) which could be selected and used to process the image to select a portion or part of the image and perform an image processing function on that selected portion or part of the image.

The image processing apparatus 100 may employ a strategy to evaluate previous episodes to reduce a computational load of the apparatus 100 and to improve, for example, a response time of the apparatus 100. For example, one strategy may be to prioritize the most similar and plausible previous episodes.

For each retrieved episode, the image processing apparatus 100 executes a preprocessing operation (PP) 314. The preprocessing operation 314 also receives the input data (DAT) 304 comprising raw image data and meta data and user input data (INP) 306 representative of user input such as gestures or other interactions between the user and the image processing apparatus 100. The user input data may include user input characteristics of the user input such as a location of the input in the first image, a shape of an input gesture, and/or a dimension of an input gesture. The user input data may also include image characteristics of the image such as a dimension of the image, display characteristics of the image and/or display characteristics in a selected part of the image. The preprocessing operation 314 prepares the data it receives for further evaluation. In particular, the preprocessing operation 314 may determine a set of processing algorithms which may be applied to the image in order to determine an action based on the received user input.

Examples of processes performed in the preprocessing operation 314 include image filtering (such as contrasting, windowing, blurring and sharpening operations) and automatic segmentation operations for identifying region of interests, such as region growing operations and edge detection operations. For example, the preprocessing operation may be an operation to remove bone features from an image, or more generally to subtract or fuse features of an image. In other examples, the preprocessing operation may register the image with a previously acquired image. In other examples, the preprocessing operation may label pixels; for example, the preprocessing operation may label pixels according to the part of a patients anatomy (i.e. pixels may be labelled as being tissue from e.g. the brain, heart, abdomen, lungs, bone, blood vessel etc.) In other examples, the preprocessing operation may label pixels according to whether the respective pixel is determined to be part of a tumour or not, or part of an inflamed piece of tissue or not. In other examples, the preprocessing operation may determine the type of image (e.g. whether the image is that of a patient's head or a patient's abdomen) or to determine characteristics of the patient (e.g. whether the patient is male or female and/or an adult or a child). The output of the preprocessing operation is preprocessed data (PPD) 316.

The preprocessed data 316 is used in a hypothesis evaluation operation (HYP) 318, which evaluates the data to derive or generate a probabilistic value in relation to each respective candidate action. The probabilistic value may indicate a probability that the candidate action corresponds to an intended action of the user. For example, the hypothesis evaluation operation 318 may generate plausibility values for various potential intents (i.e. possible regions of interest and corresponding actions intended by the user by user input) using heuristics corresponding to heuristics used in previous episodes. The plausibility value relates to how plausible a given hypothesis is and may be expressed in a range between zero and one, where zero represents an impossibility and one represents certainty. Values closer to zero correspond with implausible hypotheses and values closer to one correspond with plausible hypotheses.

Examples of the heuristics used in the hypothesis evaluation operation 318 include: a comparison of an expected size of the region of interest with the size of a region of interest computed using an automatic segmentation process; a comparison of an expected shape of the region of interest with the shape of a region of interest computed using an automatic segmentation process; a comparison of the shape of user gesture with the shape of a region of interest generated using an automatic segmentation process; and a comparison of expected input meta data for given intent with actual input meta data.

The hypothesis evaluation operation 318 may also determine a confidence value. The confidence values represent a degree of confidence in a particular hypothesis. Similar to the plausibility values, the confidence values may be expressed in a range between zero and one, where zero represents no confidence in the hypothesis and one represents certainty. Values closer to zero correspond with doubtful hypotheses and values closer to one correspond with convincing hypotheses.

For example, a hypothesis that user input is within a region of interest to the user may be evaluated. The plausibility of the hypothesis may be determined to be high (i.e. close to 1) if the received user input is inside a generated region of interest and may be determined to be low (i.e. close to 0) if the received user input is outside of the generated region of interest. The actual plausibility value may, for example, depend on how much of the input is inside or outside of the region of interest. However, the confidence of a particular evaluation may be high (i.e. close to 1) if the user input is received far from a boundary of the generated region of interest, and low (i.e. close to 0) if it is close to a boundary of the generated region of interest. In particular, the confidence value may be highest if the user input is received at or near the center of the generated region of interest.

The plausibility and confidence values may be combined to create a so-called plausibility measure. The hypothesis evaluation operation 318 may, for example, combine heuristic evaluations of all heuristics associated with intent candidate selected by the associative memory 308. The resulting plausibility measure may be determined using the following pseudocode:

```
PROCEDURE EvaluateEpisodeHypotheses(hypotheses):
  LET aggregated = EvaluateHypothesis(hypotheses[0]);
  FOR index = 1..( hypotheses.length-1:
    LET current = EvaluateHypothesis(hypotheses[index]);
    SET aggregated.Plausibility =
      aggregated.Plausibility * aggregated.Confidence
      + current.Plausibility * current.Confidence
      + aggregated.Plausibility * current.Plausibility
      * (1- aggregatednit.Confidence- current.Confidence)
    SET aggregated.Confidence =
      (aggregated.Confidence+ current.Confidence)
      / (1+ aggregated.Confidence* current.Confidence)
  END FOR
  RETURN aggregated
END PROCEDURE
```

A plausibility sorting operation (PL) 320, sorts the results of the hypothesis evaluation operation 318 according to the plausibility measure such that the most plausible areas of interest and corresponding action (i.e. image processing functions to be applied to the area of interest) are ranked higher in a list of hypotheses. The plausibility measure represents the plausibility of a match between a hypothesized intent and the received input data. In other words, the plausibility sorting operation 320 refines the set of processing algorithms generated by the associative memory 308 and determined by the preprocessing process 314 to provide a shortlist of the most promising candidate processing algorithms for determining the appropriate action (i.e. the most likely intended action of the user) based on the current image data and user input data and previous experience.

The plausibility measure may, for example, comprise a tuple (or other combination) of the plausibility value and the confidence value. Such a combination, which considers both the plausibility value and the confidence value, may avoid incomputability issues, which may occur, for example, when a single plausibility value, in which there is a low degree of confidence, has a value approaching zero or one. In such cases, logical conjunction or disjunction operators operating on the single plausibility value may become locked at the boundary values (zero or one).

Previously used heuristics and possible user intents (i.e. the possible regions of interest and corresponding actions that the user may have intended by user input) may be stored in the image processing apparatus 100 (i.e. encoded in the associative memory 308) prior to installation in a service environment or may be downloadable to the image processing apparatus 100 after installation, for example by downloading the data from the internet to the associative memory 308. The previously stored or downloaded associations may serve as a starting point which can be refined over time by learning, for example using the exploration module 108.

Determination of the plausibility and confidence values for each heuristic provide explanatory information which may be used by the image processing application 100 to present an explanation as to the reasoning for selecting a given area of interest and a given intent (i.e. image processing action) based on the user's user input.

The image processing apparatus 100 may also implement an exploratory process (EXPL) 322. The exploratory process 322 may select, on a random or pseudo-random basis, preprocessing steps, heuristics and other parameters to generate potential actions that otherwise would not be available to the image processing apparatus (for example, because the image processing apparatus had not experienced a particular set of inputs previously). For example, the exploratory process 322 may randomly pick a method of delineation of the region of interest based on a given user input and/or may randomly set edge thresholding values. Furthermore, the exploratory process may select random intents (i.e. image processing functions) from a group of known possible intents. Such randomly selected parameters may be evaluated along with the parameters defined for previous episodes 310 according to a selected subset of related heuristics. The exploratory process 322 enables the image processing apparatus to consider and evaluate possible actions that have not previously been experiences and therefore have not contributed to the weightings of the associative memory 114. In circumstances where an action suggested by the exploratory process 322 is determined to correspond to the intention of the user, the action may be stored in the associative memory 114 and therefore potentially increase the rate at which the image processing apparatus 100 learns.

The ratio of actions provided by considering previous episodes provided by the associative memory 114 and actions suggested by the exploratory process 322 may be fixed in some examples. In other examples, the ratio may be variable.

An intent presentation and explanation process (PRES) 324 prepares options, which may be displayed to the user via the display 120, representing the most plausible actions (i.e. the regions of interest and corresponding image processing functions).

Figure 4:
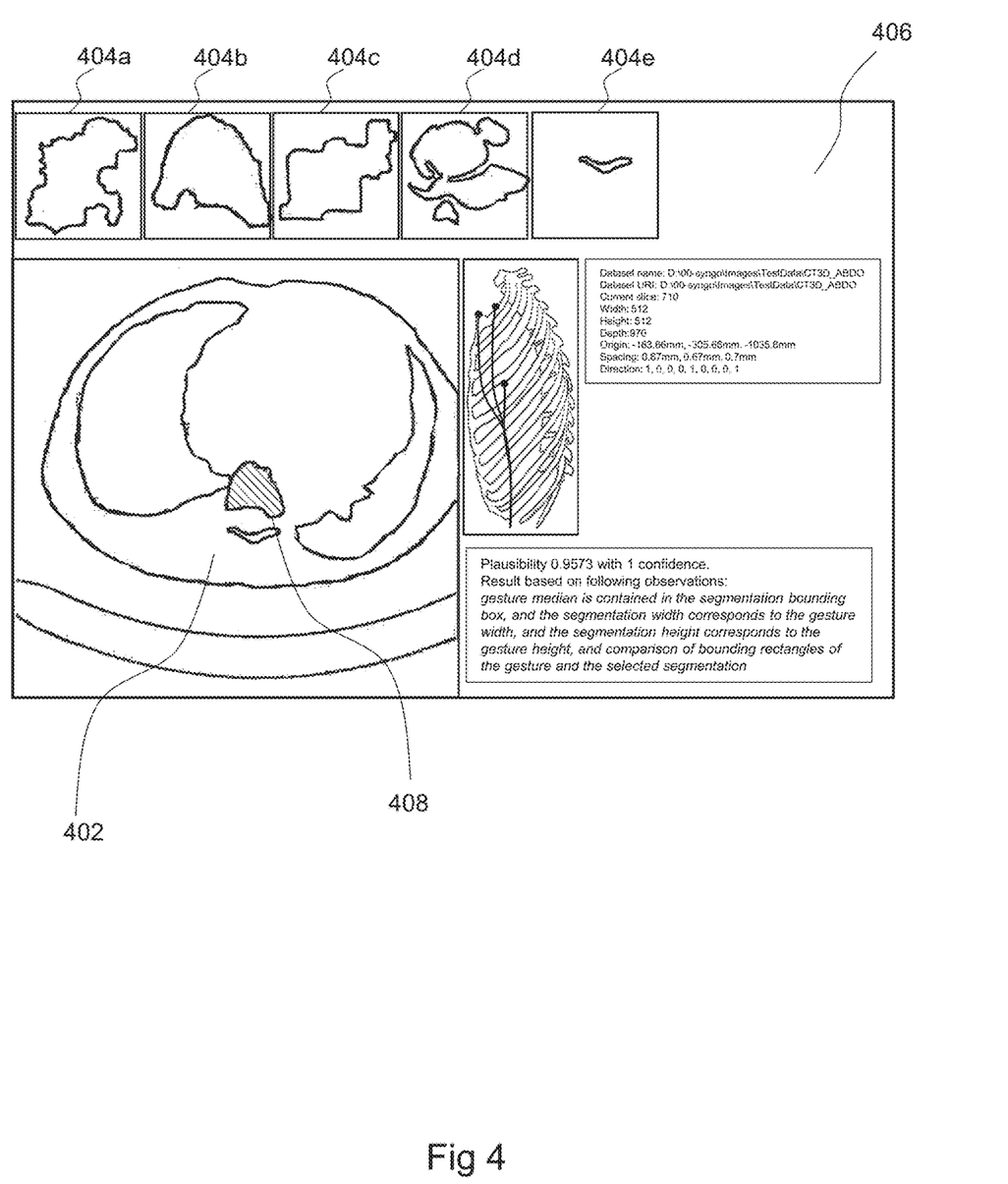
FIG. 4 is a schematic diagram illustrating an example of a user interface displayed to a user.

FIG. 4 shows an example of a user interface which may be presented to the user by the intent presentation module 110. As shown in FIG. 4, the user may be presented with the original image 402 from which they made their selection, together with one or more images representing action options 404a to 404e determined by the image processing apparatus 100 to be the most plausible candidates for actions intended by the user. In some examples, as shown in FIG. 4, the user interface may provide an overlay 406 containing information explaining to the user a reasoning for presenting each of the action options. For example, the explanation may be provided when the user moves a mouse cursor or otherwise indicates an interest in one of the displayed action options 404a to 404e. The explanation may, for example, include information relating to the plausibility and confidence values. In some examples, the user interface may highlight a region 408 of the original image 402 (indicated by a cross-hashed portion in FIG. 4) corresponding with an indicated action option 404a to 404e.

Once presented with the options 404a to 404e the user may provide feedback (FB) 326 in the form a further user input by selecting (for example with the input device as described above) to indicate the actual intent (i.e. the area of interest and action that the user intended by his initial user input). The feedback 326 is used in an execution process (EXEC) 328 to execute the action in respect of the image. In addition, the feedback 326 is fed back to the associative memory 308 to update the associative memory 308 to be used in the evaluation of future image processing operations (i.e. the user input is stored in memory as previous action data).

In some examples, if the image processing apparatus determines that there is only one available action or determines that the likelihood of a particular action option being the intent of the user is above a certain threshold, display of the action options may be omitted and the action may be carried out without further input from the user.

While the invention has been illustrated and described in detail with the help of a preferred embodiment, the invention is not limited to the disclosed examples. Other variations can be deducted by those skilled in the art without leaving the scope of protection of the claimed invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of processing a user input in relation to an image, comprising:
   receiving first input data indicating a selection of at least a first part of a first image;
   determining the at least the first part of the first image based on the first input data and previous action data relating to previous image processing actions performed in relation to one or more images;
   determining one or more candidate actions to perform in relation to at least a second part of the first image based on the first input data and previous action data indicating selected image processing actions relating to the one or more images and unselected candidate image processing actions relating to the one or more images, the determining the one or more candidate actions including,
      determining the at least the second part of the first image based on (i) previous image parts in relation to the previous action data relating to the previous image processing actions and (ii) the first input data, the second part of the first image being different than the first part of the first image or the same as the first part of the first image; and
   outputting data indicating at least a first action of the one or more candidate actions determined.

2. The method of claim 1, wherein the previous image processing actions include at least one of:
   an annotation;
   a measurement; or
   a highlighting.

3. The method of claim 2, wherein the first input data includes:
   one or more user input characteristics of the user input, the one or more user input characteristics including at least one of,
      a location of the user input in the first image,
      a shape of an input gesture, or
      a dimension of the input gesture; and
   one or more image characteristics of the at least the first part of the first image, the one or more image characteristics including at least one of,
      a dimension of the first image,
      one or more display characteristics of the first image, or
      one or more display characteristics of the at least the first part of the first image.

4. The method of claim 2, wherein the first image includes an image of a patient, and the first input data includes at least one of:
   a modality of the first image; or
   data relating to the patient.

5. The method of claim 2, wherein the determining the one or more candidate actions includes:
   identifying the previous action data by retrieving data relating to the previous image processing actions from a memory, based on the first input data;
   generating the one or more candidate actions by selecting one or more processing algorithms for processing the at least the second part of the first image; and
   evaluating the one or more candidate actions.

6. The method of claim 5, wherein the memory comprises a heterogenous associative memory.

7. The method of claim 1, wherein the first input data includes:
   one or more user input characteristics of the user input, the one or more user input characteristics including at least one of,
      a location of the user input in the first image,
      a shape of an input gesture, or
      a dimension of the input gesture; and
   one or more image characteristics of the at least the first part of the first image, the one or more image characteristics including at least one of,
      a dimension of the first image,
      one or more display characteristics of the first image, or
      one or more display characteristics of the at least the first part of the first image.

8. The method of claim 1, wherein the first image includes an image of a patient, and the first input data includes at least one of:
   a modality of the first image; or
   data relating to the patient.

9. The method of claim 1, wherein the determining the one or more candidate actions includes:
   identifying the previous action data by retrieving data relating to the previous image processing actions from a memory, based on the first input data;
   generating the one or more candidate actions by selecting one or more processing algorithms for processing the at least the second part of the first image; and
   evaluating the one or more candidate actions.

10. The method of claim 9, wherein the memory comprises a heterogenous associative memory.

11. The method of claim 10, wherein the previous action data indicates input data relating to the previous image processing actions and processing algorithms used to generate the candidate actions from the previous image processing actions, and wherein the selecting the one or more processing algorithms includes:
  comparing the first input data with input data relating to the previous image processing actions; and
  selecting one or more processing algorithms from the processing algorithms used to generate the candidate actions from the previous image processing actions based on the comparison.

12. The method of claim 10, wherein the selecting the one or more processing algorithms includes selecting the processing algorithms randomly or pseudo-randomly.

13. The method of claim 10, wherein the one or more processing algorithms includes at least one of:
  an image filter algorithm; or
  an automatic segmentation algorithm.

14. The method of claim 10, wherein the previous action data includes heuristics data relating to heuristics for evaluating the previous image processing actions, and the evaluating the one or more candidate actions includes:
  identifying one or more heuristics for evaluating a respective candidate action.

15. The method of claim 9, wherein the previous action data indicates input data relating to the previous image processing actions and processing algorithms used to generate candidate actions from the previous image processing actions, and wherein the selecting the one or more processing algorithms includes:
  comparing the first input data with the input data relating to the previous image processing actions; and
  selecting the one or more processing algorithms from the processing algorithms used to generate the candidate actions from the previous image processing actions based on the comparison.

16. The method of claim 9, wherein the selecting the one or more processing algorithms includes selecting the processing algorithms randomly or pseudo-randomly.

17. The method of claim 9, wherein the one or more processing algorithms includes at least one of:
  an image filter algorithm; or
  an automatic segmentation algorithm.

18. The method of claim 9, wherein the previous action data includes heuristics data relating to heuristics for evaluating the previous image processing actions, and the evaluating the one or more candidate actions includes:
  identifying one or more heuristics for evaluating a respective candidate action.

19. The method of claim 18, wherein the evaluating the one or more candidate actions includes:
  generating a probabilistic value in relation to each respective candidate action indicating a probability that the respective candidate action corresponds to an intended action.

20. The method of claim 19, wherein the generating the probabilistic value includes:
  generating the probabilistic value based on at least one of a plausibility value or a confidence value.

21. The method of claim 9, further comprising:
  receiving a user selection of the first action; and
  storing data relating to the first action in the memory as previous action data.

22. A non-transitory computer program product storing a computer program, loadable into a memory of a data processing system, including program code sections to make a data processing system execute the method of claim 1 when the computer program is executed in the data processing system.

23. A non-transitory computer readable medium storing a computer program, loadable and executable by a data processing system, including program code sections which, upon execution by the data processing system, cause the data processing system to perform the method of claim 1.

24. An image processing apparatus comprising:
  an associative memory configured to receive first input data indicating a selection of at least a first part of a first image and previous action data relating to previous image processing actions performed in relation to one or more images; and
  processing circuitry configured to:
    determine the at least the first part of the first image based on the first input data and the previous action data;
    determine one or more candidate actions to perform in relation to at least a second part of the first image based on the first input data and the previous action data, the previous action data indicating selected image processing actions relating to the one or more images and unselected candidate image processing actions relating to the one or more images;
    determine at least the second part of the first image based on (i) previous image parts in relation to the previous action data and (ii) the first input data, the second part of the first image being different than the first part of the first image or the same as the first part of the first image; and
    output data indicating at least a first action of the one or more candidate actions determined.

* * * * *